United States Patent
Gross et al.

[11] Patent Number: 5,186,805
[45] Date of Patent: Feb. 16, 1993

[54] ELECTROLYTIC DISPENSING DEVICE

[75] Inventors: Joseph Gross, Moshav Mazor; Shlomo Zucker, Mihmoret, both of Israel

[73] Assignee: S. I. Scientific Innovations Ltd., Kirvat Arie Petah Tikva, Israel

[21] Appl. No.: 822,798

[22] Filed: Jan. 21, 1992

[30] Foreign Application Priority Data

Jan. 30, 1991 [IL]  Israel ................................ 97099

[51] Int. Cl.$^5$ .......................... C25B 1/10; C25B 9/00; C25B 15/08
[52] U.S. Cl. .................................. 204/265; 204/266; 204/296
[58] Field of Search ..................... 204/263–266, 204/129, 256, 258, 271, 277–278

[56] References Cited

U.S. PATENT DOCUMENTS

| | | | |
|---|---|---|---|
| 807,640 | 12/1905 | Roberts | 204/266 X |
| 813,844 | 2/1906 | Van Scoyoc | 204/278 |
| 2,728,121 | 12/1955 | Goument | 204/278 X |
| 3,739,573 | 6/1973 | Giner | 60/37 |
| 3,996,126 | 12/1976 | Rasmussen | 204/271 |
| 4,902,278 | 2/1990 | Maget et al. | 604/132 |
| 4,971,669 | 11/1990 | Wrede et al. | 204/266 X |

FOREIGN PATENT DOCUMENTS 0385916  9/1990  European Pat. Off.
0389263  9/1990  European Pat. Off.

*Primary Examiner*—Donald R. Valentine
*Attorney, Agent, or Firm*—Benjamin J. Barish

[57] ABSTRACT

An electrolytic dispensing device includes a first contractible chamber for receiving a liquid to be dispensed, and a second contractible chamber for receiving a gas to control the rate of dispensing of the liquid from the first chamber. An electrolytic cell generates a gas which is fed to the second chamber to dispense liquid from the first chamber in accordance with the electrical current conducted through the electrolytic cell. The electrolytic cell includes a partition of an ion-permeable, but gas-impermeable, material separating its two electrodes. The partition is effective to permit gas generated at one electrode to be fed to the second chamber, and to block from the second chamber gas generated at the other electrode, and thereby to prevent the formation of a hazardous mixture of gases.

20 Claims, 2 Drawing Sheets

ELECTROLYTIC DISPENSING DEVICE

FIELD AND BACKGROUND OF THE INVENTION

The present invention relates to electrolytic dispensing devices, and particularly to a device for dispensing a liquid in accordance with the amount of gas generated by passing electrical current through an electrolytic cell. Electrolytic dispensing devices of this type are described, for example, in our U.S. Pat. No. 5,062,834.

Such electrolytic dispensing devices comprise a housing having a displaceable member therein dividing the interior of the housing into a first contractible chamber for receiving a liquid to be dispensed, and a second contractible chamber for receiving a gas to control the rate of dispensing of the liquid from the first chamber; and an electrolytic cell including an electrolyte and a pair of electrodes connectible to a source of electrical current for generating a gas and for feeding the gas to the second chamber in accordance with the electrical current conducted through the electrolyte via the electrodes.

It was found that the gases generated by the electrolyte may form a hazardous mixture. For example, a common electrolyte used for this purpose is a water solution of a salt or acid which generates oxygen at the anode, and hydrogen at the cathode. A mixture of these two gases could result in an explosion under extreme conditions.

OBJECTS AND BRIEF SUMMARY OF THE INVENTION

An object of the present invention is to provide an electrolytic dispensing device which avoids this hazard.

According to the present invention, there is provided an electrolytic dispensing device as set forth above, characterized in that the electrolytic cell includes a partition of an ion-permeable, but gas-impermeable, material separating the two electrodes and effective to permit gas generated at one of the electrodes to be fed to the second chamber, and to block from the second chamber gas generated at the other electrode.

An electrolytic dispensing device constructed in accordance with the foregoing features thereby provides protection against the above-mentioned hazard.

According to a preferred embodiment of the invention described below, the ion-permeable, gas-impermeable partition is a membrane of a halogenated ethylene polymer.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
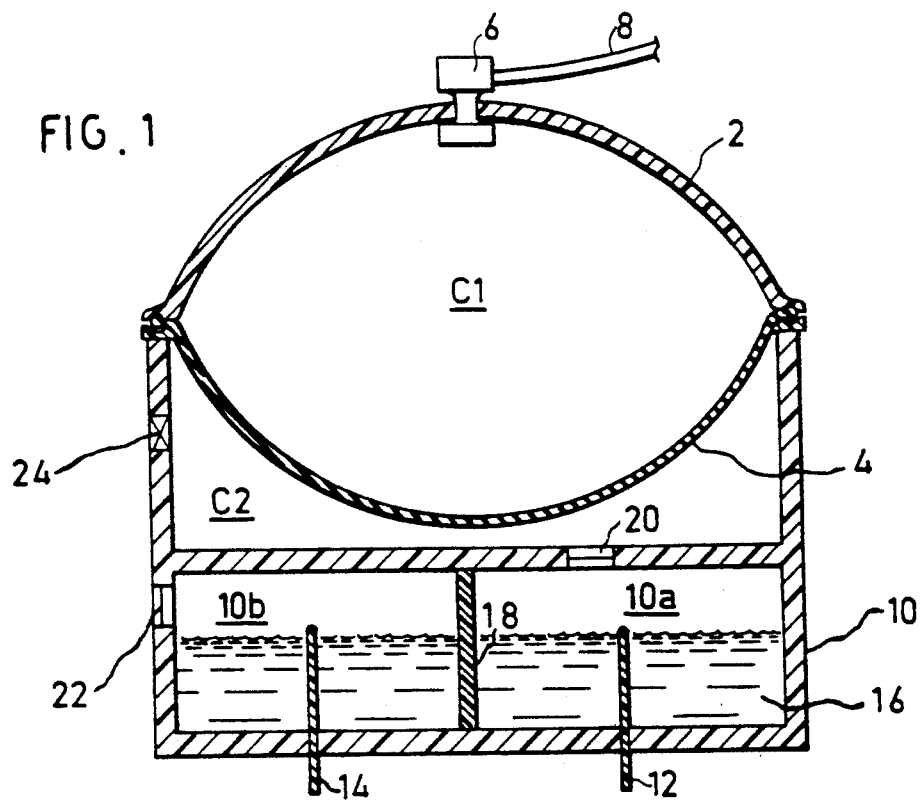
FIGS. 1-3 are transverse sectional views illustrating three electrolytic dispensing devices constructed in accordance with the present invention.

The device illustrated in FIG. 1 of the drawings comprises a rigid housing 2, having a displaceable member in the form of a flexible diaphragm 4 dividing the interior of the housing into a first contractible chamber $C_1$ and a second contractible chamber $C_2$. Chamber $C_1$ is adapted to receive a liquid to be dispensed via an outlet 6 connectible, for example, to an infusion unit via a tube 8. Chamber $C_2$ is adapted to receive a gas from an electrolytic cell 10 to control the rate of dispensing of the liquid from chamber $C_1$.

Electrolytic cell 10 includes an anode 12, a cathode 14, and an electrolyte 16 of a material which conducts electrical current between the electrodes and generates a gas in accordance with the electrical current conducted through the electrolyte. The electrodes 12, 14 are preferably stainless steel nets or screens. Preferably, water solutions of various salts or acids are used as the electrolyte 16. Examples of suitable materials are: baking soda (sodium bicarbonate), caustic soda, magnesium sulphate, potassium sulphate, sodium sulphate, potassium nitrate, potassium bicarbonate, boric acid, acetic acid, formic acid, or carbonic acid, preferably in concentrations of 2-20% by weight solution of the salts or acids. Particularly good results have been obtained where the electrolyte is an 8% solution of baking soda (sodium bicarbonate). Such water solutions release oxygen at the anode 12 and hydrogen at the cathode 14.

The electrolytic cell 10 further includes a partition 18 which divides the interior of the cell into two sections: section 10a containing the anode 12, and section 10b containing the cathode 14. Partition 18 is made of an ion-permeable but gas-impermeable material. Particularly good results have been obtained when using an ion-exchange membrane made of a tetrafluorethylene or monochloro-trifluoro-ethylene polymer, such as Teflon (Reg.T.M.) and Permion 1000 (Reg.T.M.).

The portion of the housing wall separating electrolytic cell section 10a from the gas chamber $C_2$ includes a gas-permeable, liquid-impermeable membrane 20 for feeding the gas from section 10a into the gas chamber $C_2$. The portion of the housing wall separating electrolytic cell section 10b from the atmosphere includes a similar gas-permeable liquid-impermeable membrane 22 for venting to the atmosphere the gas generated in section 10b. Preferably such membranes are of a hydrophobic material, such as Nylon Acrodisc (Reg.T.M.) having passage holes of about 2 inches.

The portion of housing 2 which separates gas chamber $C_2$ from the atmosphere is provided with a shut-off valve, shown schematically at 24, which may be opened in order to discharge the gas from chamber $C_2$ to the atmosphere.

The dispensing device illustrated in FIG. 1 operates as follows: The two electrodes 12, 14 are connected to a source of electrical current (e.g., a battery, not illustrated) to cause electrical current to flow through the electrolyte 16 separating the two electrodes. As a result of such electrical current, oxygen is generated at the anode 12 in the cell section 10a, and hydrogen is generated at the cathode in the cell section 10b. The ion-permeable partition 18 permits the flow of ions through the partition, but blocks the flow of gas therethrough. As a result, the oxygen generated in cell section 10a is permitted to pass via the gas-permeable membrane 20 into the gas chamber $C_2$ to dispense liquid from the liquid chamber $C_1$ via outlet 6 in accordance with the amount of gas generated. However, the hydrogen generated in cell section 10b is blocked by partition 18 from flowing via cell section 10a into the gas chamber $C_2$. Such hydrogen can therefore only flow via the gas-permeable membrane 22 to the atmosphere.

Accordingly, the dispensing device illustrated in FIG. 1 will dispense a liquid from chamber $C_1$ in accordance with the amount of electrical current conducted through the electrolyte 16, but will prevent the hydrogen generated at the cathode 14 from mixing with the oxygen generated at the anode 12, and will thereby avoid the hazard of producing an explosive mixture of such gases.

Figure 2:
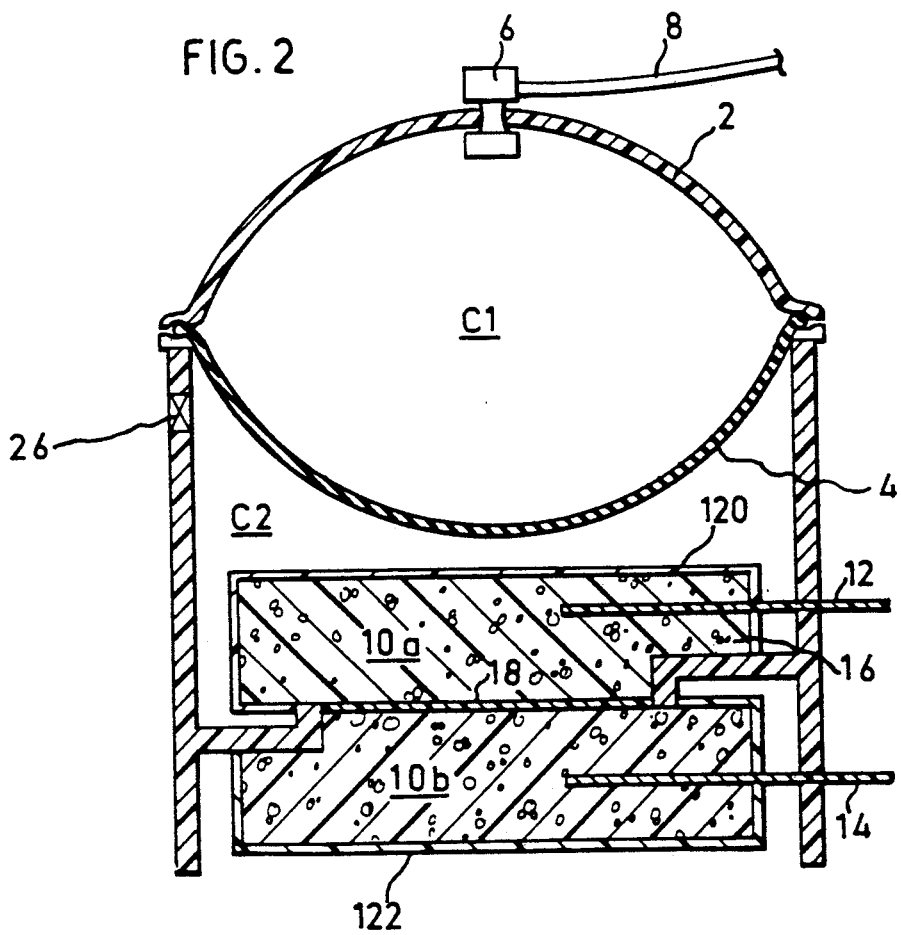

FIG. 2 illustrates a dispensing device of similar construction as in FIG. 1, and carries the same numbers as the corresponding parts in FIG. 1 to facilitate understanding. The main difference in the device of FIG. 2 over that of FIG. 1 is in the construction of the two gas-permeable, liquid-impermeable membranes 20, 22.

Thus, whereas in the device of FIG. 1 the gas-permeable, liquid-impermeable membrane 20 is located in the wall of the housing separating cell section 10a from the gas chamber $C_2$, in the construction of FIG. 2 this membrane, therein designated 120, constitutes the complete wall of the electrolytic cell section 10a. Similarly, whereas in the FIG. 1 construction the gas-permeable, liquid-impermeable membrane 22 is in the wall between the electrolytic cell section 10b and the atmosphere, in the construction of FIG. 2 this membrane, therein designated 122, constitutes the complete wall between electrolytic cell section 10b and the atmosphere.

As shown in FIG. 2, electrolytic cell section 10b containing the cathode 14 is located below electrolytic cell section 10a containing the anode 12. In addition, the two electrodes 12, 14 pass through the side wall of the housing 2, rather than through its bottom wall. In all other respects, the device illustrated in FIG. 2 is constructed and operates substantially the same as described above with respect to FIG. 1.

In the constructions of both of FIGS. 1 and 2, the electrolyte 16 may be in a flowable body, e.g., one of the water solutions mentioned above. Alternatively, such an electrolyte may also be in a non-flowable body, e.g., in the form of a gel or an impregnant of a microporous plastic or rubber body.

Figure 3:
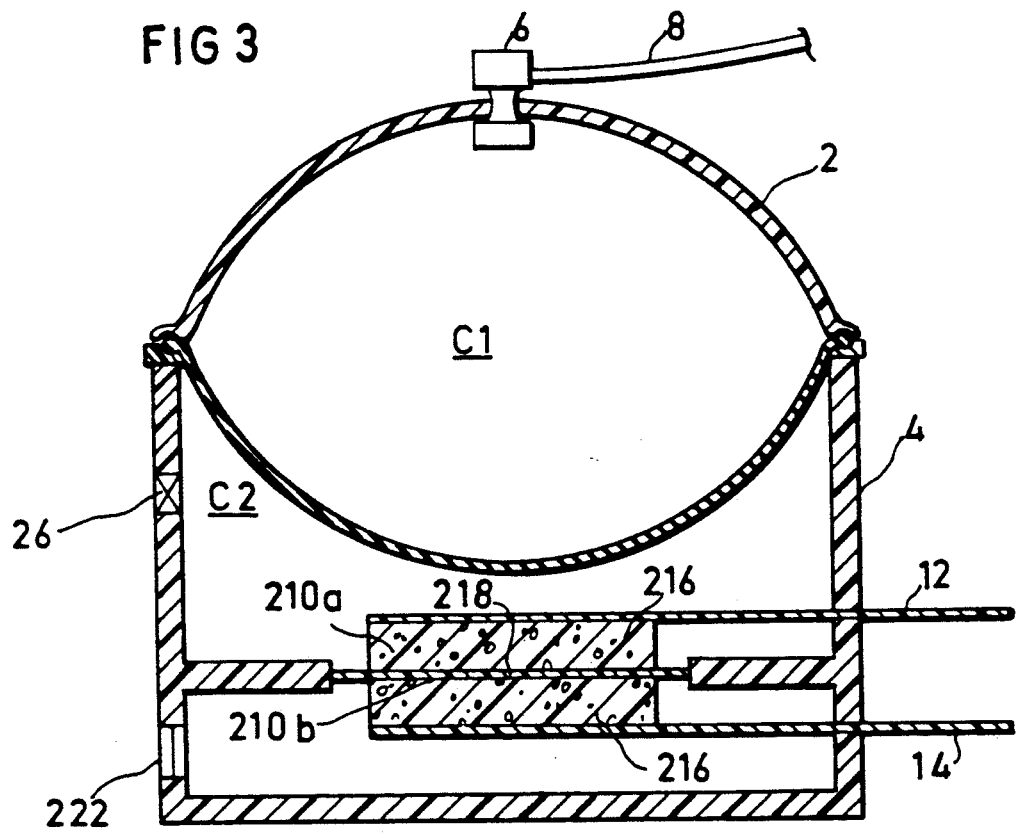

FIG. 3 illustrates a construction particularly useful where the electrolyte, therein designated 216, is in the form of one of the latter non-flowable bodies. In this case, electrolytic cell section 210a defined by the partition 218 communicates directly with, and is actually disposed in, the gas chamber $C_2$, and therefore does not require a gas-permeable, liquid-impermeable membrane, such as shown at 20 in FIG. 1 or 120 in FIG. 2. Electrolytic cell section 210b, however, communicates with the atmosphere via a gas-permeable liquid-permeable membrane, as shown at 222 in FIG. 3. In all other respects, the device illustrated in FIG. 3 is constructed and operates substantially the same as described above with respect to FIGS. 1 and 2.

While the invention has been described with respect to several preferred embodiments, it will be appreciated that these are set forth merely for purposes of example, and that many other variations, modifications and applications of the invention may be made.

What is claimed is:

1. An electrolytic dispensing device, comprising: a housing having a displaceable member therein dividing the interior of the housing into a first contractible chamber for receiving a liquid to be dispensed, and a second contractible chamber for receiving a gas to control the rate of dispensing of the liquid from said first chamber; and an electrolytic cell adapted to contain an electrolyte, said cell including a pair of electrodes connectible to a source of electrical current for generating a gas and for feeding the gas to the second chamber in accordance with the electrical current conducted through the electrolyte via the electrodes; characterized in that said electrolytic cell includes a partition of an ion-permeable, but gas-impermeable, material separating said two electrodes and effective to permit gas generated at one of said electrodes to be fed to said second chamber, and to block from said second chamber gas generated at said other electrode.

2. The device according to claim 1, wherein said partition is an ion-exchange membrane.

3. The device according to claim 2, wherein said ion-permeable, gas-impermeable membrane is a halogenated ethylene polymer.

4. The device according to claim 1, wherein the electrolytic cell includes a gas-permeable, liquid-impermeable membrane for feeding to said second chamber the gas generated at said one electrode.

5. The device according to claim 4, wherein the electrolytic cell includes a second gas-permeable, liquid-impermeable membrane for venting to the atmosphere the gas generated at said other electrode.

6. The device according to claim 5, wherein said ion-permeable partition divides the electrolytic cell into a first section containing said one electrode and having a first wall separating said first section from said second chamber, and a second section containing said other electrode and having a second wall separating said second section from the atmosphere; said first-mentioned gas-permeable membrane being carried by said first wall, and said second gas-permeable membrane being carried by said second wall.

7. The device according to claim 6, wherein said first and second walls are made of said gas-permeable membranes.

8. The device according to claim 1, wherein said electrolytic cell further includes an electrolyte in the form of a non-flowable body.

9. The device according to claim 1, wherein said displaceable member is a flexible diaphragm.

10. The device according to claim 1, wherein the gases generated in the electrolytic cell are oxygen and hydrogen, and said ion-permeable, gas-impermeable partition blocks the flow of the hydrogen to the second chamber.

11. An electrolytic dispensing device, comprising: a housing having a displaceable member therein dividing the interior of the housing into a first contractible chamber for receiving a liquid to be dispensed, and a second contractible chamber for receiving a gas to control the rate of dispensing of the liquid from said first chamber; and an electrolytic cell adapted to contain an electrolyte, said cell including a pair of electrodes connectible to a source of electrical current for generating a gas and for feeding the gas to the second chamber in accordance with the electrical current conducted through the electrolyte via the electrodes; said electrolytic cell including a partition of an ion-exchange, gas-impermeable, membrane separating said two electrodes and effective to permit gas generated at one of said electrodes to be fed to said second chamber, and to block from said second chamber gas generated at said other electrode.

12. The device according to claim 11, wherein the electrolytic cell includes a gas-permeable, liquid-impermeable membrane for feeding to said second chamber the gas generated at said one electrode.

13. The device according to claim 12, wherein the electrolytic cell includes a second gas-permeable, liquid-impermeable membrane for venting to the atmosphere the gas generated at said other electrode.

14. The device according to claim 13, wherein said ion-permeable membrane divides the electrolytic cell into a first section containing said one electrode and having a first wall separating said first section from said second chamber, and a second section containing said other electrode and having a second wall separating said second section from the atmosphere; said first-mentioned gas-permeable membrane being carried by said first wall, and said second gas-permeable membrane being carried by said second wall.

15. The device according to claim 14, wherein said first and second walls are made of said gas-permeable membrane.

16. The device according to claim 14, wherein said gas-permeable membranes are of hydrophobic material.

17. The device according to claim 11, wherein said electrolytic cell further includes an electrolyte in the form of a non-flowable body.

18. The device according to claim 11, wherein said displaceable member is a flexible diaphragm.

19. The device according to claim 11, wherein the gases generated in the electrolytic cell are oxygen and hydrogen, and said ion-permeable, gas-impermeable membrane blocks the flow of the hydrogen to the second chamber.

20. The device according to claim 19, wherein said ion-permeable, gas-impermeable membrane is a halogenated ethylene polymer

* * * * *